United States Patent
Liu

(10) Patent No.: US 9,687,376 B2
(45) Date of Patent: *Jun. 27, 2017

(54) KNEE BRACE HAVING THREE STIMULATORS FOR CONTINUAL ELECTRO-ACUPUNCTURAL STIMULATION; IN VIVO AND IN SITU TISSUE ENGINEERING

(71) Applicant: Y. King Liu, Pataluma, CA (US)

(72) Inventor: Y. King Liu, Pataluma, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/987,549

(22) Filed: Aug. 6, 2013

(65) Prior Publication Data

US 2013/0331750 A1   Dec. 12, 2013

Related U.S. Application Data

(63) Continuation-in-part of application No. 13/694,662, filed on Dec. 24, 2012, and a continuation-in-part of
(Continued)

(51) Int. Cl.
- *A61N 1/05* (2006.01)
- *A61F 5/01* (2006.01)
(Continued)

(52) U.S. Cl.
CPC .......... *A61F 5/0123* (2013.01); *A61F 5/0106* (2013.01); *A61N 1/0452* (2013.01); *A61N 1/0456* (2013.01); *A61N 1/0484* (2013.01); *A61N 1/0502* (2013.01); *A61N 1/36017* (2013.01); *A61N 1/36021* (2013.01)

(58) Field of Classification Search
CPC .............. A61N 1/0502; A61N 1/36017; A61N 1/36021
See application file for complete search history.

(56) References Cited

U.S. PATENT DOCUMENTS

| 5,211,184 A | 5/1993 | Yee et al. |
| 5,273,033 A | 12/1993 | Hoffman |

(Continued)

*Primary Examiner* — Eric D. Bertram
(74) *Attorney, Agent, or Firm* — Our Pal Asija; Suganda Jutamulia; Raman Guntaka

(57) ABSTRACT

A knee brace for continual electro-acupuncture stimulation system comprises a first circuit having a first circuit having a first electrode configured to electrically coupled to acupuncture point "Heting (S 156)" and a second electrode configured to electrically coupled to acupuncture point "Bladder 40", a second circuit having a third electrode configured to electrically coupled to acupuncture point "Spleen 10" and a fourth electrode configured to electrically coupled to acupuncture point "Hsiyen (S 145)", and a third circuit having a fifth electrode configured to electrically coupled to acupuncture point "Stomach 34" and a sixth electrode configured to electrically coupled to acupuncture point "Stomach 35". The first, third, and fifth electrodes are connected to a polarity of voltage, and the second, fourth, and sixth electrodes are connected to an opposite polarity of voltage, such that electric currents flow in a body of a patient to achieve analgesia, cartilage repair and regeneration in the knee joint.

12 Claims, 3 Drawing Sheets

Related U.S. Application Data application No. 12/626,034, filed on Nov. 25, 2009, now Pat. No. 9,440,069, and a continuation of application No. 11/747,075, filed on May 10, 2007, now abandoned.

(60) Provisional application No. 60/799,263, filed on May 10, 2006.

(51) Int. Cl.
*A61N 1/36* (2006.01)
*A61N 1/04* (2006.01)

(56) References Cited

U.S. PATENT DOCUMENTS

| | | |
|---|---|---|
| 5,324,287 A | 6/1994 | Szeles |
| 5,792,171 A | 8/1998 | Burdenko et al. |
| 6,231,584 B1 | 5/2001 | Gavronsky |
| 2004/0044390 A1 | 3/2004 | Szeles |
| 2005/0177201 A1 | 8/2005 | Freeman |
| 2006/0079946 A1 | 4/2006 | Gavronsky et al. |
| 2006/0085047 A1 | 4/2006 | Unsworth et al. |
| 2011/0082515 A1* | 4/2011 | Libbus et al. .......... 607/44 |
| 2013/0110220 A1* | 5/2013 | Brown .......... 607/149 |

* cited by examiner

KNEE BRACE HAVING THREE STIMULATORS FOR CONTINUAL ELECTRO-ACUPUNCTURAL STIMULATION; IN VIVO AND IN SITU TISSUE ENGINEERING

CROSS-REFERENCE TO RELATED APPLICATIONS

This application claims priority under 35 U.S.C. §120 as a continuation-in-part application of U.S. patent application Ser. No. 13/694,662 filed on Dec. 24, 2012, which claims priority under 35 U.S.C §120 as a continuation-in-part application of U.S. patent application Ser. No. 12/626,034 filed on Nov. 25, 2009, which claims priority under 35 U.S.C. §120 as a continuation application of U.S. patent application Ser. No. 11/747,075 filed on May 10, 2007, which in turn claims priority under 35 U.S.C. §119 to U.S. Provisional Application No. 60/799,263, filed May 10, 2006. The disclosure of all priority applications is hereby incorporated by reference in their entireties.

FIELD OF THE INVENTION

This invention relates to continual electro-acupunctural stimulation and more specifically to knee braces having three stimulators for continual electro-acupunctural stimulation for in vivo and in situ therapeutic effects on analgesia and tissue regeneration and repair.

BACKGROUND OF THE INVENTION

In China, the insertion of acupuncture needles into acupuncture points to treat diseases has been practiced for at least 2,000 years. The addition of electricity or electro-acupuncture was documented in a French text as early as in 1825. Its author, Chevalier Solardiere, claimed that when static electricity, generated by rubbing a silk scarf against ebony was discharged into the inserted acupuncture needles, the electrical discharge enhanced the therapeutic results of acupuncture. In the 1950's, Chinese acupuncture practitioners used an automobile starter motor as a continuous source of electrical stimuli to acupuncture needles to enhance the efficacy and efficiency of the acupuncture therapeutic effects. Since that original motor-starter stimulator, various electronic stimulators have been employed with a plethora of therapeutic claims. The stimuli delivered by these stimulators to the acupuncture points through the acupuncture needles have varied in frequency, voltage, current, pulse shape and duration. The duration of the electrical stimuli is generally very brief, such as ranging from 10 to 60 minutes. One such system and method can be found in U.S. Pat. No. 7,200,444 to Gavronsky et al., herein incorporated by reference in its entirety.

SUMMARY OF THE INVENTION

According to one embodiment of the invention, a knee brace for continual electro-acupuncture stimulation system comprises a first circuit having a first electrode configured to electrically coupled to acupuncture point "Heting (S 156)" and a second electrode configured to electrically coupled to acupuncture point "Bladder 40", a second circuit having a third electrode configured to electrically coupled to acupuncture point "Spleen 10" and a fourth electrode configured to electrically coupled to acupuncture point "Hsiyen (S 145)", and a third circuit having a fifth electrode configured to electrically coupled to acupuncture point "Stomach 34" and a sixth electrode configured to electrically coupled to acupuncture point "Stomach 35". The first, third, and fifth electrodes are connected to a polarity of voltage, and the second, fourth, and sixth electrodes are connected to an opposite polarity of voltage, such that electric currents flow in a body of a patient to achieve analgesia, cartilage repair and regeneration in the knee joint.

According to one embodiment of the invention, the electrodes of the knee brace are connected to external controller units enclosing a battery for supplying electric currents, a switch for turning the electric power of the battery on and off, and an electro stimulator for modulating the electric currents supplied by the battery.

BRIEF DESCRIPTION OF THE DRAWINGS

The invention is further illustrated in the following Figures.

DETAILED DESCRIPTION OF THE PREFERRED EMBODIMENT

Disclosed herein are devices and methods for analgesia and tissue repair and regeneration that does not require major surgery or a research-intensive stem cell approach and, at the same time, it is a non-invasive fast-acting treatment. The disclosed treatment is inexpensive when compared to surgical treatments. This recent biomedical breakthrough is a vast improvement over current treatment modalities, whether measured by cost or by time-to-heal effectiveness.

According to some embodiments of the invention, disclosed is a set of electrodes applied externally to certain selected acupuncture points for treating osteoarthritis including pain, joint stiffness, limitation of range of motion and limitation of overall function through the use of sub-sensory unidirectional voltage or current pulses. The electrical stimulus can be applied, in one embodiment, through electrodes of three stimulators disposed onto the appropriate anatomical points of the patient such that it is close to the cartilaginous surfaces of an osteoarthritic joint. The electrotherapeutic stimulation restores the normal electromagnetic field enveloping the joint. For the cartilage tissue, the field stimulates chondrocyte functioning, and increases synthesis of proteoglycans and Type II collagen molecules in cartilage resulting in the efficient and efficacious repair of damaged cartilage. The devices and methods disclosed herein can be more efficient and efficacious than, for example, transcutaneous electrical stimulation through non-specifically placed surface electrodes. Articular cartilage and fibrocartilage repair can potentially take place after three to four weeks of continuous treatment.

Most current treatments for advanced osteoarthritis involve surgically invasive interventions, such as total knee replacement or total hip replacement. These treatments are costly and for some they can be quite perilous in terms of patient morbidity and mortality. Post surgical recovery requires significant time and total joint replacement surgery presents complications or compromised functionality for about 10% of patients. There are few alternative treatments that have shown effectiveness compared to conservative as well as standard surgical practices. Those that do exist require months of treatment. To the contrary, the device and method shown can provide a fast-acting non-invasive alternative treatment that works continuously or substantially continuously and, in most cases, will permit daily patient ambulation, which will further patient rehabilitation.

Figure 1A:
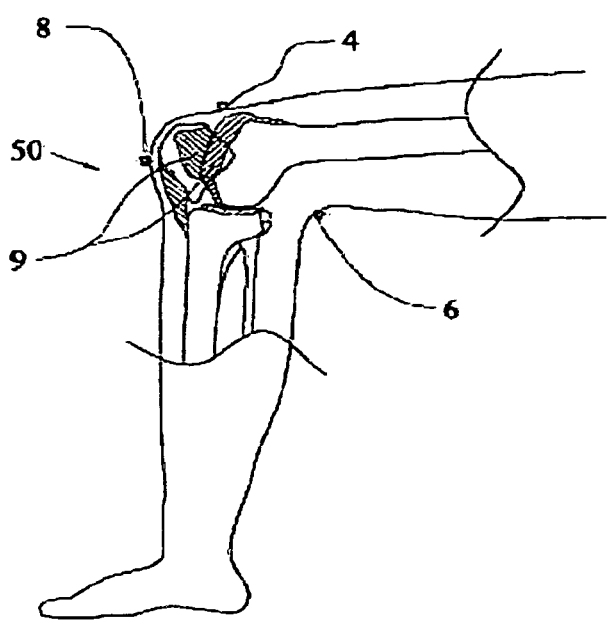
FIGS. 1A-1B show an overview of the continual electro-acupuncture stimulation system applied to produce analgesia, repair and/or regeneration of cartilage in the knee joint.
Figure 1B:
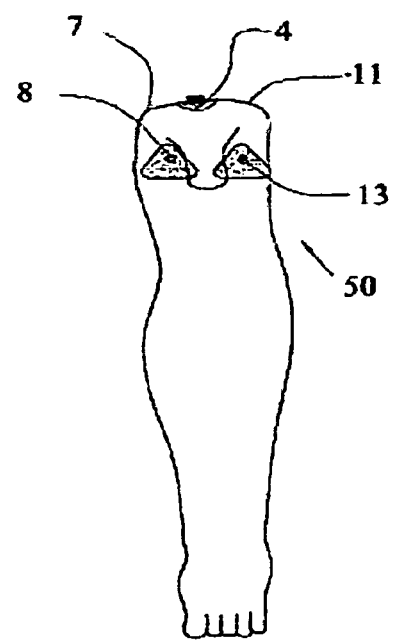

FIGS. 1A-1B illustrates some possible advantageous locations to produce analgesia, repair and/or regeneration of cartilage 9 in the knee joint 50. FIG. 1A is a lateral schematic view of the knee 50 illustrating acupuncture points "Hsiyen (S 145) point", also known as "eye of the knee" 8, "Heting point (S 156)" 4, and "Bladder 40" 6. FIG. 1B is a frontal schematic view of the knee illustrating other advantageous acupuncture points for knee analgesia, repair, and/or regeneration of cartilage, such as "Hsiyen (S 145)" 8, "Spleen 10" 7, "Heting point (S156)" 4, "Stomach 34" 11, and "Stomach 35" 13. These points can be located by one of ordinarily skill in the art as described below:

"Hsiyen (S 145)" 8: Locate this point with knee flexed, at the lower border of the patella in the depression lateral to the patellar ligament.

"Stomach 34" 11: Locate this point with knee flexed, two finger-widths (comparable to the patients fingers size) above the medio-superior border of the patella on the bulge of the medial portion of the quadriceps femoris muscle.

"Stomach 35" 13: Locate this point in the depression, medial to the patellar ligament, locating the point with the knee flexed.

"Spleen 10" 7: Locate this point with the knee flexed, measure two thumb widths (comparable to the patients thumb size) above the latero-superior border of the patella.

"Heting (S 156)" 4: Locate this point at the depression of the midpoint of the superior patellar border.

"Bladder 40" 6: Locate this point at the midpoint of the transverse crease of the popliteal fossa, between the tendons of the biceps femoris and semitendinosus muscles.

The nature and location of various points and meridians used in Chinese acupuncture are described in many texts, such as the following; the book "Acupuncture in Medical Practice", Louise O. Wensel, M. D., published 1980 by Reston Publishing (A Prentice Hall Company) is particularly noted; the book "Acupuncture, The Ancient Chinese Art of Healing and How it Works Scientifically", Felix Mann, M. B. published 1973 by Vintage Books, a division of Random House, New York; the book "Chinese Acupuncture and Moxibustion", Revised Edition, Chief Editor Cheng Xinnong published 1999 by Foreign Languages Press, Beijing, and; the book "A Manual of Acupuncture" by Peter Deadman et al. published 2001 by Journal of Chinese Medicine Publications. All of these four texts are herein incorporated by reference in their entirety. Appropriate corresponding anatomical landmarks can be selected in order to produce the desired clinical result.

Figure 2:
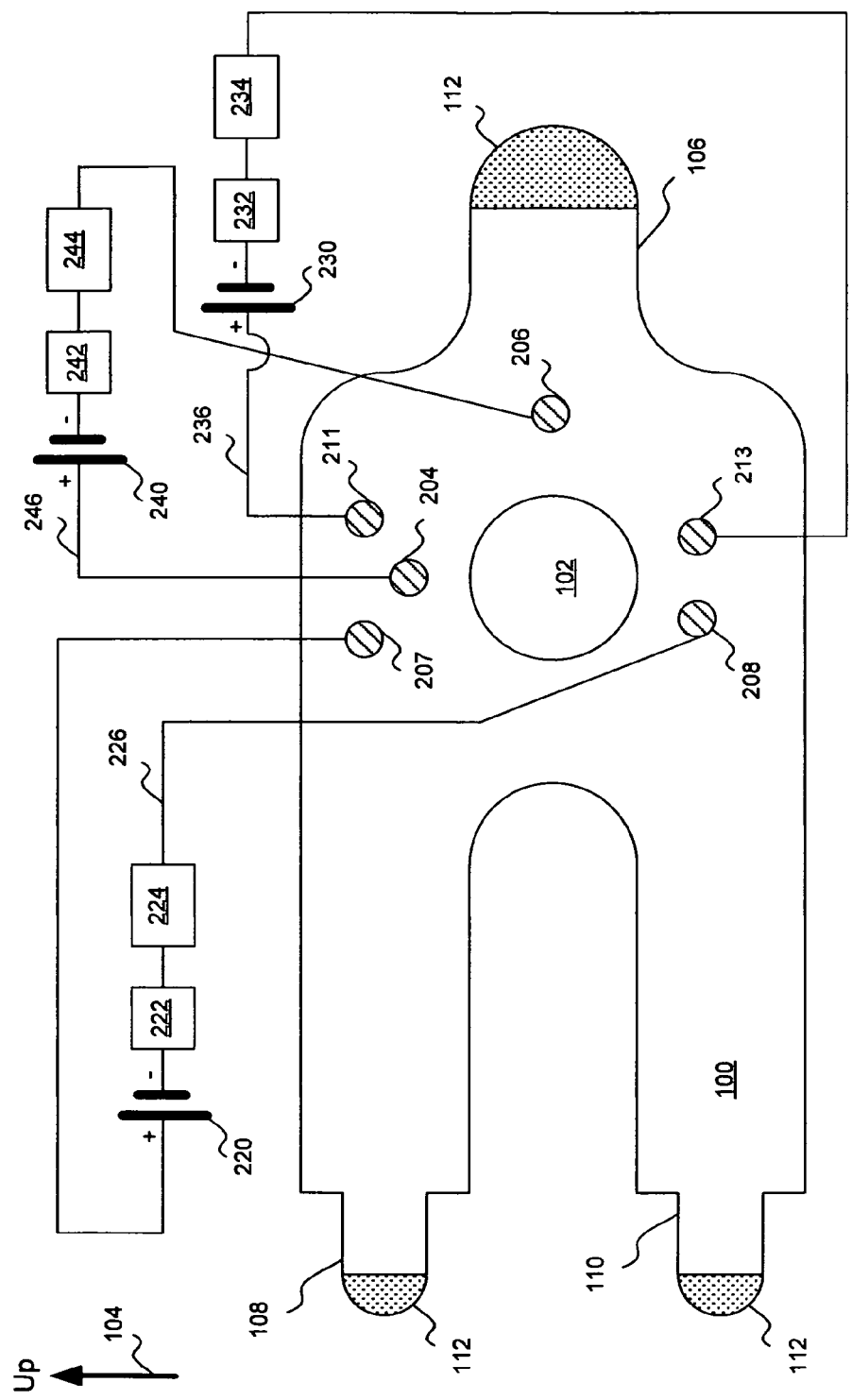
FIG. 2 illustrates a schematic diagram of a knee brace for continual electro-acupuncture stimulation system, according to an embodiment of the invention.

FIG. 2 shows a schematic diagram of a knee brace 100 having three stimulators for continual electro-acupuncture stimulation system, according to an embodiment. Knee brace 100 has a patella-shaped hole 102 for anchoring the knee brace to the knee joint of a patient when knee brace 100 is fixed to the knee. Knee brace is fixed referring to an arrow 104 showing the up direction of the knee. Knee brace 100 comprises non-invasive electrodes 204, 207, 211, 208, 213, and 206.

When knee brace 100 is fixed to the knee: electrode 204 is configured to electrically coupled to acupuncture point "Heting (S 156)" 4; electrode 207 is configured to electrically coupled to acupuncture point "Spleen 10" 7; electrode 211 is configured to electrically coupled to acupuncture point "Stomach 34" 11; electrode 208 is configured to electrically coupled to acupuncture point "Hsiyen (S 145)" 8; electrode 213 is configured to electrically coupled to acupuncture point "Stomach 35" 13; electrode 206 is configured to electrically coupled to acupuncture point "Bladder 40" 6.

In an embodiment, knee brace 100 comprises three individual stimulators 224, 234, and 244 in circuits 226, 236, and 246, respectively, as shown in FIG. 2. Electrodes 207 and 208 are included in circuit 226. Electrodes 211 and 213 are included in circuit 236. Electrodes 204 and 206 are included in circuit 246. The polarity of electrodes 207, 211, and 204 may be positive or negative. Accordingly, the polarity of electrodes 208, 213, and 206 may be negative or positive.

Circuit 226 may include a battery 220 or batteries for supplying electric currents that flow through electrode 207 to electrode 208. Circuit 226 may also include a switch 222 for turning the electric power of battery 220 on and off. The electric current from battery 220 is modulated by an electro stimulator 224. The electric current modulated by electro stimulator 224 is flowing through electrode 207 into the body of a patient to achieve analgesia, cartilage repair and regeneration in the knee joint. The current is then collected from electrode 208 back to circuit 226.

Circuit 236 may include a battery 230 or batteries for supplying electric currents that flow through electrode 211 to electrode 213. Circuit 236 may also include a switch 232 for turning the electric power of battery 230 on and off. The electric current from battery 230 is modulated by an electro stimulator 234. The electric current modulated by electro stimulator 234 is flowing through electrode 211 into the body of the patient to achieve analgesia, cartilage repair and regeneration in the knee joint. The current is then collected from electrode 213 back to circuit 236.

Circuit 246 may include a battery 240 or batteries for supplying electric currents that flow through electrode 204 to electrode 208. Circuit 246 may also include a switch 242 for turning the electric power of battery 240 on and off. The electric current from battery 240 is modulated by an electro stimulator 244. The electric current modulated by electro stimulator 244 is flowing through electrode 204 into the body of the patient to achieve analgesia, cartilage repair and regeneration in the knee joint. The current is then collected from electrode 208 back to circuit 246.

The electrodes may be made of conducting rubber, conducting silicone, or the like, or metal. In an embodiment, closed circuits 226, 236, and 246 may be embedded internally inside the knee brace.

In an embodiment, when knee brace 100 is fixed to the knee, and the electric power is turned on by switch 222, the electric current flows from acupuncture point "Spleen 10" 7 to acupuncture point "Hsiyen (S 145)" 8 in circuit 226. When the electric power is turned on by switch 232, the electric current flows from acupuncture point "Stomach 34" 11 to acupuncture point "Stomach 35" 13 in circuit 236. When the electric power is turned on by switch 242, the electric current flows from acupuncture point "Heting (S 156)" 4 to acupuncture point "Bladder 40" 6 in circuit 246. The currents are inside the body of the patient to achieve analgesia, cartilage repair and regeneration in the knee joint.

Knee brace 100 has at least one strap to fix it to the knee. For example, knee brace 100 may have three straps 106, 108, and 110 to wrap around knee brace 100 for fixing knee brace 100 to the knee. Straps 106, 108, and 110 may have fastening components 112 for fastening knee brace 100. Fastening components 112 may be a hook-and-loop fastener material, such as Velcro.

Figure 3:
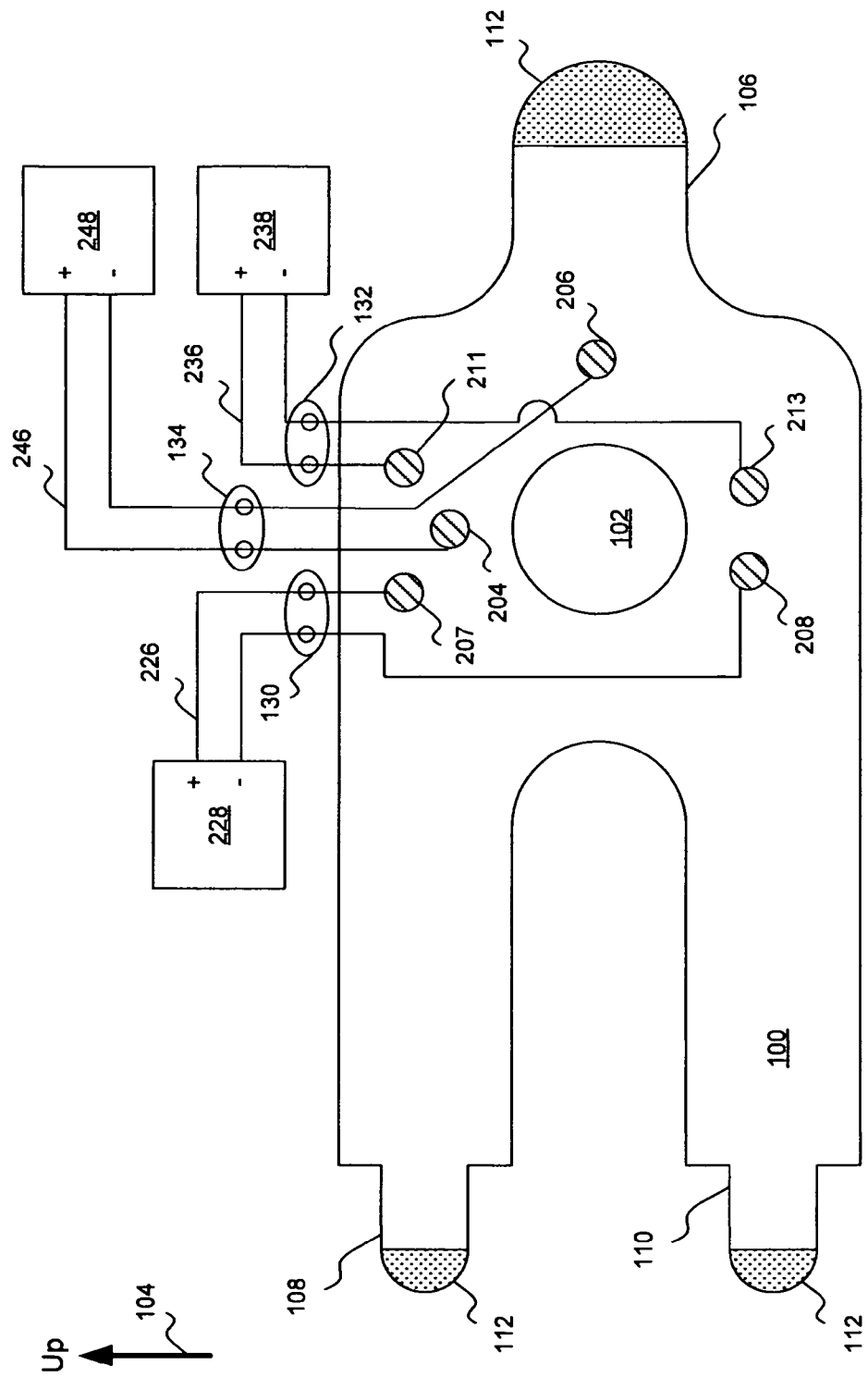
FIG. 3 illustrates a schematic diagram of a knee brace for continual electro-acupuncture stimulation system having a controller unit external to the brace, according to an embodiment of the invention.

FIG. 3 shows an embodiment where controller units 228, 238, and 248, disposed externally to knee brace 100, according to the disclosure. Controller unit 228 includes battery 220, switch 222, and electro stimulator 224 (not shown). Controller unit 238 includes battery 230, switch 232, and electro stimulator 234 (not shown). Controller unit 248 includes battery 240, switch 242, and electro stimulator 244 (not shown). Other parts of FIG. 3 are the same as FIG. 2. Controller units 228, 238, and 248 may be disposed in a pocket or pockets on knee brace 100.

Controller unit 228 may be connected to circuit 226 through a connector 130. Controller 238 may be connected to circuit 236 through a connector 132. Controller 248 may be connected to circuit 246 through a connector 134. In some implementation, wires connecting to controller units may be long enough for keeping controller units far from knee brace 100, for example, keeping controller units in a pocket or pockets of shirt, dress, or pant worn by the patient. Wires from electrodes to connectors may be embedded in knee brace 100, and only connectors 130, 132, and 134 may be extending from knee brace 100.

One of ordinary skill in the art will readily appreciate that a wide variety of fastening materials can be substituted for hook-and-loop fastener material for any or all of the disclosed components. Such fastening materials include, for example, snap fasteners, button fasteners, adhesives, tapes, buckle fasteners, locks, magnetic fasteners, custom made orthotics, and the like.

In some embodiments, electrical stimulators 224, 234, and 244 can have the following settings: 0-5 milliamp current, 0-18V voltage, 1-100 Hz frequency, 1-99% duty cycle. The pulse waveform is preferably square; however, other morphologies such as triangular, sinusoidal, sawtooth, spike, j-spike, and the like can also be used depending on the desired clinical result. Electrical stimulators 224, 234, and 244 are preferably battery powered; however, they could also be powered by AC outlet using an adaptor (not shown). The battery may be rechargeable. In an embodiment, a square wave of 2 Hz frequency may be applied.

However, it is to be understood that the above construction is only an idealization for ease of illustration, and in reality any of the components could vary in any one or more or any combination of size, shape, size distribution, shape distribution, or other geometric or orthotic characteristics.

In one embodiment, a patient with a disease to be treated, such as osteoarthritis of the knee, is selected. A general overall health assessment for electrotherapy, a focused gait examination, and a Visual Analog Scale (VAS) pain assessment is conducted to better assess the patient's pre-treatment pain. The patient can receive diagnostic bi-planar X-rays and/or Tesler 3 or 7 magnetic resonance imaging (MRI) exams with a patient body weight preload. If the patient is determined to be a suitable candidate, treatment is commenced by fixing the knee brace to patient's knee. In one embodiment, the electrodes at points "Heting (S156)" 4, "Spleen 10" 7, and "Stomach 34" 11 serve as positive electrodes. The electrodes at points "Bladder 40" 6, "Stomach 35" 13, and "Hsiyen (S145)" 8 serve as negative electrodes. In another embodiment, the polarity may be reversed.

The electrodes are operably connected to the electrical stimulator. The power of the stimulator is then increased to a threshold level of sensation by the patient, and then decreased to a sub-sensory level for patient comfort, as well as potentially advantageously promoting analgesia and cartilage repair and/or remodeling. In an embodiment, the practitioner will be able to determine with an appropriate treatment duration depending on the desired clinical result and patient progress through regular serial follow-up visits, physical examinations, pain assessments, radiographs and/or MRIs. In an embodiment, the patient may self-administer the use of the device.

In some embodiments, the electrical stimulator power remains above a threshold sensory level during treatment. In other embodiments, the stimulator power remains sub-sensory throughout the time the electrodes are operably connected to the stimulator. In still other embodiments, the stimulator power can cycle between sensory and sub-sensory power levels during treatment. Candidates for total joint replacement may benefit by undergoing nearly continuous stimulation over an extended period of time. In some embodiments, the system is left in place for 2-5 weeks as a therapeutic trial before contemplating more invasive surgical procedures. In some embodiments, the system can be applied for at least about 1, 2, 3, 5, 7, 10, 14, 21, 28, 35, 42, 60, 90, 120 or more days depending upon the desired clinical result. The various fastening mechanisms disclosed herein can advantageously assist in providing secure implantation of the system for extended periods of time.

The electrical stimulator may be turned on continuously for 24 hours each day. However, in some embodiments, it may be preferable that the electrical stimulator be only activated for only a portion of each day, for example, at least about 1, 2, 3, 4, 6, 8, 10, 12, 14, 16, 18, 20 hours or more each day, and not be active when the patient is more actively moving the area to be treated in activities such as standing, walking, sleeping, or the like. In some embodiments, the electrical stimulator may have a mercury switch automatically that turns off the stimulator when the patient stands and resumes stimulation when the patient is seated or in a recumbent position. In other embodiments, the stimulator can be turned on and off manually.

In an embodiment, knee brace 100 comprises only one of circuits 226, 236, and 246. In another embodiment, knee brace 100 comprises only two of circuits 226, 236, and 246.

While the present invention has been described herein with respect to the exemplary embodiments and the best mode for practicing the invention, it will be apparent to one of ordinary skill in the art that many modifications, improvements and sub-combinations of the various embodiments, adaptations and variations can be made to the invention without departing from the spirit and scope thereof. For the disclosed methods, the steps need not necessarily be performed sequentially.

The terms used in the following claims should not be construed to limit the invention to the specific embodiments disclosed in the specification and the claims. Rather, the scope is to be determined entirely by the following claims, which are to be construed in accordance with established doctrines of claim interpretation. The present specification and figures are accordingly to be regarded as illustrative rather than restrictive.

What is claimed is:

1. A knee brace for continual electro-acupuncture stimulation system, comprising:
a knee brace;

a first circuit having a first electrode configured to electrically couple to acupuncture point "Heting (S 156)" and a second electrode configured to electrically couple to acupuncture point "Bladder 40";

a second circuit having a third electrode configured to electrically couple to acupuncture point "Spleen 10" and a fourth electrode configured to electrically couple to acupuncture point "Hsiven (S 145)"

a third circuit having a fifth electrode configured to electrically couple to acupuncture point "Stomach 34" and a sixth electrode configured to electrically couple to acupuncture point "Stomach 35"; and wherein the first, third, and fifth electrodes are simultaneously connected to a first polarity of voltage, and the second, fourth, and sixth electrodes are simultaneously connected to a second polarity of voltage that is opposite the first polarity, wherein each electrode is attached to the knee brace at a location that simultaneously couples each electrode to its respective acupuncture point when the knee brace is fixed to a knee of a patient such that electric currents flow in a body of a patient to achieve analgesia, cartilage repair and cartilage regeneration in the knee joint.

2. The knee brace of claim 1, wherein the first circuit comprising:
a battery for supplying electric currents;
a switch for turning an electric power of the battery on and off;
an electro-stimulator for modulating the electric currents supplied by the battery.

3. The knee brace of claim 1 further comprising at least one strap to wrap around the knee brace for fixing the knee brace to a knee of a patient.

4. The knee brace of claim 3 further comprising a fastening component.

5. The knee brace of claim 4 wherein the fastening component includes a hook-and-loop fastener material.

6. The knee brace of claim 1 further comprising a patella shaped hole for anchoring the knee brace to a knee joint of a patient.

7. The knee brace of claim 1, wherein the electrodes are made of one of conducting rubber, conducting silicone, and metal.

8. The knee brace of claim 1, wherein the electrodes are non-invasive.

9. The knee brace of claim 1, wherein the knee brace is externally connected to a first controller unit comprising:
a battery for supplying electric currents;
a switch for turning an electric power of the battery on and off;
an electro stimulator for modulating the electric currents supplied by the battery; and
wires for connecting to a connector.

10. The knee brace of claim 9, wherein wires connecting the connector and the electrodes are embedded in the knee brace, and wherein the connector is extending from the knee brace.

11. The knee brace of claim 1, wherein the second circuit comprising:
a battery for supplying electric currents;
a switch for turning an electric power of the battery on and off;
an electro-stimulator for modulating the electric currents supplied by the battery.

12. The knee brace of claim 1, wherein the third circuit comprising:
a battery for supplying electric currents;
a switch for turning an electric power of the battery on and off;
an electro-stimulator for modulating the electric currents supplied by the battery.

* * * * *